(12) United States Patent
Seth

(10) Patent No.: US 6,338,857 B1
(45) Date of Patent: Jan. 15, 2002

(54) SUSTAINED RELEASE CARBAMAZEPINE PHARMACEUTICAL COMPOSITION FREE OF FOOD EFFECT AND A METHOD FOR ALLEVIATING FOOD EFFECT IN DRUG RELEASE

(75) Inventor: Pawan Seth, Irvine, CA (US)

(73) Assignee: Pharma Pass LLC, Irvine, CA (US)

( * ) Notice: Subject to any disclaimer, the term of this patent is extended or adjusted under 35 U.S.C. 154(b) by 0 days.

(21) Appl. No.: 09/579,391

(22) Filed: May 26, 2000

(51) Int. Cl.[7] ................................................ A61K 9/20
(52) U.S. Cl. .................. 424/464; 424/468; 424/469; 424/470; 424/474; 424/480; 424/488
(58) Field of Search ................................ 424/439, 468, 424/474, 488, 464, 490, 471, 451, 452, 457, 461, 462, 470, 469, 480

(56) References Cited

U.S. PATENT DOCUMENTS

| | | | |
|---|---|---|---|
| 5,378,474 A | 1/1995 | Morella et al. | |
| 5,529,791 A | 6/1996 | Deboeck et al. | |
| 5,580,578 A | 12/1996 | Oshlack et al. | |
| 5,879,714 A | 3/1999 | Sherman | |
| 6,048,547 A | * 4/2000 | Seth et al. ................ | 424/464 |

OTHER PUBLICATIONS

D. Benziger et al., Journal of Pharmaceutical Sciences, vol. 85, No. 4, Apr. 1996, pp. 407–410.

* cited by examiner

Primary Examiner—Thurman K. Page
Assistant Examiner—Blessing Fubara
(74) Attorney, Agent, or Firm—Harness, Dickey & Pierce, P.L.C.

(57) ABSTRACT

The invention provides a sustained release composition free of food effect comprising:

(c) a core comprising carbamazepine; and
(d) a functional coating comprising, based on the weight of the coating, from 30 to 80% of a gastroresistant polymer and from 10 to 40% of a hydrophilic silicon dioxide.

The invention also provides a method for alleviating food effect in a carbamazepine pharmaceutical composition.

16 Claims, 1 Drawing Sheet

SUSTAINED RELEASE CARBAMAZEPINE PHARMACEUTICAL COMPOSITION FREE OF FOOD EFFECT AND A METHOD FOR ALLEVIATING FOOD EFFECT IN DRUG RELEASE

BACKGROUND OF THE INVENTION

Food effect is a well-known phenomenon that can adversely affect the pharmacokinetics of drug distribution in the body. As a result, many drugs have to be taken either in fasted or fed conditions to achieve the optimum effect. Well known examples include carbamazepine tablets (to be taken with meals), captopril tablets (to be taken one hour before meals), or azithromycin tablets (to be taken 2 hours after meal), while some other drugs remain unaffected by food, as amoxicillin for example.

For this reason, FDA recommends to test bioequivalency of drug products either under fasted or fed conditions, depending on the drug. Moreover, in the latter case the meal itself is standardized.

Little formulation work has been conducted to date in order to overcome this food effect disadvantage.

U.S. Pat. No. 5,529,791 describes an extended release formulation of diltiazem pellets coated with either cellulosic or synthetic polymers, and absence of food effect is reported. However, no link is explained between the composition of the product and the absence of food effect.

Benziger et al., J.Pharm.Sci., 85,4, pp.407–410 (1996) compared the bioavailability of oxycodone formulated as an immediate release aqueous solution or as extended release tablets, under fasted or fed conditions and found a significant difference in availability of the solution while no difference could be observed with the extended release tablets. These authors related the absence of food effect to the use of extended release tablets rather than to any specific formulation parameter.

U.S. Pat. No. 5,879,714 a drug and a water insoluble polymer are mixed into a molten carrier, preferably water-soluble. The only example provided in this patent consists in melting PEG 8000 at 120° C. and dispersing nifedipine, stearic acid and Eudragit RSPO in it. After cooling, the solidified mixture is ground into granules. Heat sensitivity of many drugs seems is a major concern when considering applying the process thereto. Absence of food effect is not disclosed but it is indicated that hydrophilic matrix systems are said to be more likely to induce food effect than the disclosed formulation.

U.S. Pat. No. 5,580,578 provides controlled release formulation having a coating consisting essentially in methacrylic copolymers, said coating having been oven cured. Examples disclose compositions comprising a core comprising thee active ingredient (e.g. hydromorphone hydrochloride), an intermediate layer comprising hydroxypropylmethylcellulose and the cured overcoat based on Eudragit. After oven curing, drug products tested clinically were found to be exempt of food effect (this was however not justified by formulation parameters). The coating is comprised of sustained release acrylic copolymers of the type Eudragit RS (comprising optionally Eudragit RL).

None of the above documents teaches or suggests the present invention.

SUMMARY OF THE INVENTION

The invention relates to a novel sustained release pharmaceutical composition that is free or devoid of food effect and to a method for alleviating the food effect in the drug release.

The invention thus provides a sustained release composition free of food effect comprising:

(a) a core comprising an active ingredient; and
(b) a functional coating comprising, based on the weight of the coating, from 30 to 80% of a gastroresistant polymer and from 10 to 40% of a hydrophilic silicon dioxide.

The instant invention also provides a process for alleviating food effect in a pharmaceutical composition, comprising the step of coating a core comprising an active ingredient with a functional coating comprising, based on the weight of the coating, from 30 to 80% of a gastroresistant polymer and from 10 to 40% of a hydrophilic silicon dioxide.

DETAILED DESCRIPTION

Figure 1:
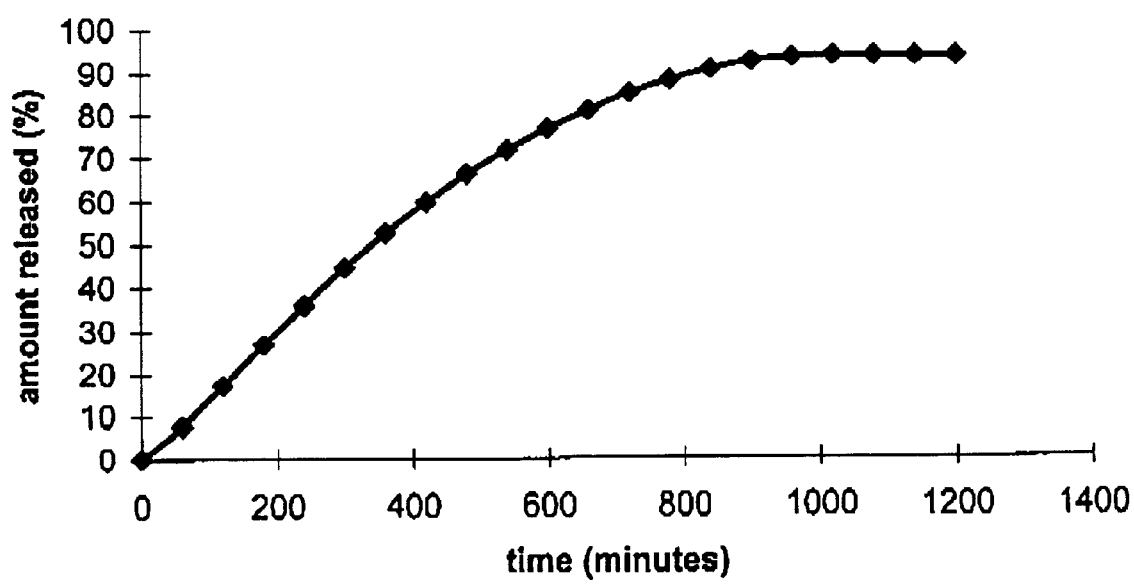
FIG. 1 is the release curve of carbamazepine compositions in a sodium laurylsulfate/phosphate buffer medium.

The present invention consists in a coated tablet.

The core of said tablet comprises one or several pharmacologically active substances chosen among those of which absorption is known to be influenced by food intake. Examples of such drugs comprise carbamazepine, verapamil, nifedipine, felodipine, amlodipine, diltiazem, oxibutynin, doxazocin, venlafaxin, captopril, enalapril, fenofibrate, without being restricted to them.

The core usually comprises from 20 to 80% of active ingredient. It also generally comprises 10 to 80% by weight of a gelling agent, which can be chosen among hydroxypropylmethylcellulose, hydroxypropylcellulose, carboxymethylcellulose, xanthan gum, carbomer, carragheen, polyethyleneglycol and polyethylene oxide. The core additionally comprises classical excipients, like (microcristalline) cellulose, lubricants, silicon dioxide, desintegrating agents, etc.

The core may be obtained by preparing a mixture of the starting compounds and direct compression. Alternatively, the gelling agent and the active ingredient are granulated together, and the resulting granules, optionally with other excipients, are compressed into a tablet.

Surprisingly, it has been discovered that the coating of the composition presents the unique feature of preventing the whole dosage form from being influenced by food intake.

This coating comprises a functional coating which comprises, based on the weight of the coating, from 30 to 80% of a gastroresistant polymer and from 10 to 40% of a hydrophilic silicon dioxide.

The gastroresistant polymer withstands the acidic medium of the stomach and the duodenum, but will dissolve in the intestines, as soon as the pH reaches a predetermined level (e.g. above 5.5 or above 7). This gastroresistant polymer can be selected from the group consisting in (uncured) poly(meth)acrylic acid, cellulose and alkylcellulose-phtalates. Molecular weight can vary within broad limits as will recognize the skilled man. The term "uncured" is used to differentiate over U.S. Pat. No. 5,580,578.

Preferably, it is of the type of Eudragit L30D55. One preferred polymer is an anionic copolymer on the basis of methacrylic acid and acrylic acid ethyl ester. The formula is as follows:

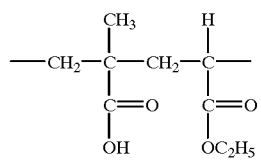

The ratio free carboxyl group to ester group is preferably about 1:1. The mean molecular weight is e.g. about 250,000.

Such a copolymer will easily dissolve at pH values above 5.5 with the forming of salts.

Hydrophilic silicon dioxide is a known hydrophilic antitacking agent, the definition of which is known to the skilled man and can be found in the literature.

The functional coating may further comprise polyethyleneglycol, present in an amount from 5 to 30% by weight, based on the total weight of the functional coating. Stearic acid, dibutyl sebacate, propylene glycol and/or triethyl citrate can used in lieu of or in addition to polyethyleneglycol.

The functional coating usually represents from 0.5 to 6% by weight of the core weight.

The composition may further comprise an intermediate coating.

This coating which acts as a protecting layer comprises classical excipients, such as those recited above with respect to the core. For example, this intermediate coating comprises hydroxypropylmethylcellulose and polyethyleneglycol. This intermediate coating usually represents from 0.1 to 3% by weight of the core weight. In the case of a layer comprised of HPMC and PEG, the weight ratio HPMC:PEG is e.g. from 2 to 10.

The composition of the invention is a sustained release; preferably it provides an effective release of the active ingredient for a period of at least 8 hours, preferably at least 12 hours.

The invention is also concerned with a process for alleviating food effect in a pharmaceutical composition, comprising the step of coating a core comprising an active ingredient with the functional coating as defined above.

Thanks to the invention, it is now possible to avoid the food effect for virtually any drug. The invention makes it possible to operate with any drug, since the process does not involve any heating step, in contrast with the prior art.

Finally, the invention concerns a composition that is the precursor of the functional coating. Thus, the invention also provides an aqueous dispersion (suspension) of a gastroresistant polymer and of a hydrophilic silicon dioxide, present according to a weight ratio gastroresistant polymer:hydrophilic silicon between 0.75:1 and 8:1.

The dispersion (suspension) typically has a solid content from 3 to 50% by weight, e.g. about 10%.

The suspension may further comprise polyethyleneglycol dissolved in it, in an amount up to 15% by weight.

PREFERRED EMBODIMENTS

One preferred embodiment is a tablet comprising:
(a) a core comprising carbamazepine;
(b) a first layer comprising HPMC and polyethyleneglycol; and
(c) a second layer comprising a methacrylic copolymer, hydrophilic silicon dioxide and polyethyleneglycol.

EXAMPLES

The following examples illustrate the invention without limiting it.

Example 1

Carbamazepine.

The following core formulation was prepared

| Ingredient | Amount per dosage unit (mg) |
|---|---|
| Carbamazepine | 400.00 |
| Aerosil 200 ® | 3.00 |
| Avicel PH 302 ® | 100.00 |
| Plasdone K90 ® | 8.00 |
| Denatured alcohol | 290.00 |
| Methocel K 100 LV ® | 125.00 |
| Sodium stearylfumarate | 17.00 |

Carbamazepine and Methocel® are mixed to Avicel and 50% of the amount of Aerosil 200® passed through a 0.5 mm mesh size sieving screen. Plasdone® is dissolved in ethanol. The powder mixture is put into a mixer and wet with the solution. The resulting agglomerates are passed through a sieving screen of 0.062" (Co Mill®). Granules are dried to constant weight in an oven at 45° C. (loss on drying with infrared balance=1.5%). Dry granules are mixed to sodium stearyl fumarate and Aerosil 200® in drum mixer (Turbula® T2C). The resulting mixture is pressed into tablets of 657 mg and about 150 N hardness, using a Manesty Betapress® tableting machine fitted with 12 mm diameter punches.

These tablet cores were then coated with an intermediate coating of the following composition:

| Ingredient | Amount per dosage unit (mg) |
|---|---|
| Pharmacoat 603 ® | 5.50 |
| Polyethyleneglycol 1450 | 1.00 |
| Purified water | 50.00 |

Pharmacoat 603®is HPMC, available from Shin-Etsu chemicals. Pharmacoat 603 and PEG 1450 are dissolved in water and the solution is sprayed onto the tablet cores in a Vector coating pan, using the following spraying parameters:

| Inlet Air Temperature | 55–60 C. |
|---|---|
| Outlet Air Temperature | 40–45 C. |
| Spray Rate | 5–8 g/minute |
| Spray Pressure | 30 psi |
| Pan Speed | 16 rpm |

These coated tablets were then coated a second time with a functional coating of the following composition:

| Ingredient | Amount per dosage unit (mg) |
|---|---|
| Eudragit ® L30D55 | 13.30 (Solid) |
| Syloid ®244FP | 4.00 |
| Polyethyleneglycol 8000 | 2.70 |
| Purified water | 80.00 |

Eudragit® L30D55 is a methacrylic copolymer available from Rohm. The 13.30 value represents the weight of the solids and not the weight of the dispersion.

PEG 8000 is dissolved in 45% of amount of purified water. This solution is added to Eudragit suspension and stirred with paddle stirrer for 45 minutes. Syloïd® 244FP is suspended in the remaining part of water and the suspension is homogenized with a high-speed homogenizer Ultra Turrax® T25. The two suspensions are mixed and the mixture is sprayed onto the tablets in a Vector coating pan, using the following parameters:

| Inlet Air Temperature | 55–60 C. |
|---|---|
| Outlet Air Temperature | 40–45 C. |
| Spray Rate | 5–8 g/minute |
| Spray Pressure | 30 psi |
| Pan Speed | 16 rpm |

This coating is uncured, since no oven is used once the coating has been applied.

These tablets are tested for dissolution in standard apparatus type 1 of United States Pharmacopoeia. A 2% solution of sodium laurylsulfate in 0.01M potassium dihydrogenophosphate pH 6.8 buffer is used as dissolution medium. The amount of carbamazepine dissolved is recorded vs. time by using a Hewlett Packard HP8452A spectrophotometer. The curve is given in FIG. 1. It can be seen that the composition provides an effective release of carbamazepine during about 12 hours.

For the clinical trials, this formulation was tested against the same Tegretol® XR, reference product from Novartis® in a two way cross study performed on 6 healthy volunteers. To get an evaluation of the efficiency of the coating, tablets of the above formulation were also tested against tablets of the same composition except that the functional coating was replaced by a classical (cosmetic) coating of the following composition:

| Ingredient | Amount per dosage unit (mg) |
|---|---|
| Opadry ® | 15.00 |
| Purified water | 80.00 |

Opadry® comprises HPMC, HPC, titanium dioxide and PEG; it is available from Coloron.

Classical pharmacokinetics parameters Cmax and AUC were recorded, where:

Cmax is the maximal plasma concentration reached during the study; and

AUC is the area under the plasmatic concentration vs. time curve.

Results presented in table are ratios of parameters between test and reference products. Reference product is Tegretol®. Table 1 gives the results for the classical tablet while table 2 gives the results for the tablet of the invention.

TABLE 1

|  | $Cmax_{ref}/Cmax_{test}$ | $AUC_{ref}/AUC_{test}$ |
|---|---|---|
| Fasted conditions | 1.01 | 0.99 |
| Fed conditions | 1.48 | 1.26 |

TABLE 2

|  | $Cmax_{ref}/Cmax_{test}$ | $AUC_{ref}/AUC_{test}$ |
|---|---|---|
| Fasted conditions | 1.03 | 1.06 |
| Fed conditions | 1.07 | 1.03 |

From the above tables, it is clear that the classical tablet has a marked food effect while the tablet of the invention are free of any food effect.

Example 2

Verapamil

In a manner similar as above, the following formulation was prepared.

Core:

| Ingredient | Amount per dosage unit (mg) |
|---|---|
| Verapamil HCl | 240.00 |
| Avicel PH 101 | 25.00 |
| Plasdone K30 ® | 20.00 |
| HPMC 15,000 cPs | 35.00 |
| HPMC 100 cPs | 20.00 |
| Silicon dioxide | 1.50 |
| Magnesium stearate | 3.50 |

HPMC is hydroxypropylmethylcellulose.

Coating:

| Ingredient | Amount per dosage unit (mg) |
|---|---|
| Eudragit ® L30D55 | 7.50 |
| Syloid ®244FP | 3.00 |
| PEG 1450 | 1.50 |

Example 3

Oxibutynin

In a manner similar as above, the following formulation was prepared.

Core:

| Ingredient | Amount per dosage unit (mg) |
|---|---|
| Oxibutynin HCl | 15.00 |
| Avicel PH 101 | 24.50 |
| Plasdone K30 ® | 10.00 |
| Polyox WSR | 180.00 |
| Silicon dioxide | 3.00 |
| Sodium stearyl fumarate | 6.00 |
| Vitamin E | 2.00 |

Coating:

| Ingredient | Amount per dosage unit (mg) |
|---|---|
| Eudragit ® L30D55 | 5.55 |
| Fumed silica | 2.20 |

-continued

| Ingredient | Amount per dosage unit (mg) |
|---|---|
| PEG 1450 | 1.10 |
| Triethyl citrate | 0.55 |

Fumed silica is hydrophilic silicon dioxide available from Grace Chemicals.

Triethyl citrate is a plasticizer.

The dissolution profile has been determined (medium is 750 ml phosphate buffer pH=6.8, basket 100 rpm). The results are the following:

| Time (hr) | % dissolved |
|---|---|
| 1 | 11 |
| 2 | 20 |
| 4 | 38 |
| 6 | 54 |
| 8 | 70 |
| 10 | 83 |
| 12 | 99 |

What is claimed is:

1. A sustained release composition free of food effect comprising:
    (a) a core comprising 20 to 80% of carbamazepine and 10 to 80% of hydroxypropylmethylcellulose;
    (b) an intermediate coating; and
    (c) a coating comprising from 30 to 80% of a gastroresistant polymer and from 10 to 40% of a hydrophilic silicon dioxide.

2. The composition according to claim 1, in which the gastroresistant polymer is selected from the group consisting in uncured poly(meth)acrylic acids, cellulose and alkylcellulose-phtalates.

3. The composition according to claim 1, in which the coating (c) further comprises polyethyleneglycol, present in an amount from 5 to 30% by weight, based on the total weight of the coating.

4. The composition according to claim 1, in which the coating (c) represents from 0.5 to 6% by weight of the core weight.

5. The composition according to claim 1, in which the core is comprised of granules compressed together.

6. The composition according to claim 1, in which the intermediate coating comprises hydroxypropylmethylcellulose and polyethyleneglycol.

7. A sustained release composition free of food effect comprising:
    (a) a core comprising 20 to 80% of carbamazepine and 10 to 80% of hydroxypropylmethylcellulose;
    (b) an intermediate coating; and
    (c) a coating comprising from 30 to 80% of a gastroresistant polymer comprising uncured poly(meth)acrylic acids and from 10 to 40% of a hydrophilic silicon dioxide.

8. The composition according to claim 7, in which the coating (c) further comprises polyethyleneglycol, present in an amount from 5 to 30% by weight, based on the total weight of the coating.

9. A sustained release composition free of food effect comprising:
    (a) a core comprising 20 to 80% of carbamazepine and 10 to 80% of hydroxypropylmethylcellulose;
    (b) an intermediate coating comprising hydroxypropylmethylcellulose and polyethylene-glycol; and
    (c) a coating comprising from 30 to 80% of a gastroresistant polymer comprising uncured poly(meth)acrylic acids, from 10 to 40% of a hydrophilic silicon dioxide and from 5 to 30% by weight of polyethyleneglycol.

10. The composition according to claim 1, providing effective release of the active ingredient for a period of at least 8 hours.

11. The composition according to claim 7, providing effective release of the active ingredient for a period of at least 8 hours.

12. The composition according to claim 9, providing effective release of the active ingredient for a period of at least 8 hours.

13. A process for alleviating food effect in a pharmaceutical composition, comprising steps of coating a core comprising carbamazepine with an intermediate layer and coating the intermediate layer with a coating comprising, based on the weight of the coating, from 30 to 80% of a gastroresistant polymer and from 10–40% of an hydrophilic silicon dioxide.

14. The process of claim 13, wherein the core comprises from about 20 to about 80% by weight carbamazepine and from about 10% to about 80% by weight hydroxypropylmethylcellulose.

15. The process of claim 13, wherein the gastroresistant polymer comprises uncured poly(meth)acrylic acids.

16. The process of claim 13, wherein the coating further comprises from about 5% to about 30% by weight polyethyleneglycol.

* * * * *